(12) United States Patent
Ronnberg et al.

(10) Patent No.: US 6,613,032 B2
(45) Date of Patent: Sep. 2, 2003

(54) PRODUCTS, WHICH PRODUCTS ARE ABSORBENT OR CAN ACT AS SUPPORTS FOR ABSORBENT ARTICLES

(75) Inventors: Peter Ronnberg, Mölndal (SE); Cecile Sandin, Mölndal (SE); Ingemar Fernfors, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/901,681

(22) Filed: Jul. 11, 2001

(65) Prior Publication Data

US 2002/0022819 A1 Feb. 21, 2002

Related U.S. Application Data

(60) Provisional application No. 60/217,480, filed on Jul. 11, 2000.

(51) Int. Cl.[7] ............... A61F 13/20; A61F 13/15; A41B 9/00
(52) U.S. Cl. ............... 604/385.03; 604/389; 604/391; 2/400
(58) Field of Search ............... 604/386–391, 604/385.03, FOR 103, 104; 2/400–408, 219, 235

(56) References Cited

U.S. PATENT DOCUMENTS

| | | | |
|---|---|---|---|
| 4,699,622 A | 10/1987 | Toussant et al. | |
| 4,846,815 A | 7/1989 | Scripps | |
| 5,221,274 A | * 6/1993 | Buell et al. | ........... 604/358 |
| 5,423,789 A | 6/1995 | Kuen | |
| 5,605,735 A | 2/1997 | Zehner et al. | |
| 6,030,373 A | * 2/2000 | VanGompel et al. | ........ 24/442 |
| 6,099,516 A | * 8/2000 | Pozniak et al. | ............ 2/300 |
| 6,142,986 A | * 11/2000 | Lord et al. | ............. 604/386 |
| 6,210,389 B1 | * 4/2001 | Long et al. | ............. 24/442 |

FOREIGN PATENT DOCUMENTS

| | | |
|---|---|---|
| EP | 0 719 534 | 7/1996 |
| EP | 0 696 911 | 1/1997 |
| EP | 0 893 115 | 1/1999 |
| GB | 2 303 821 | 4/1997 |
| WO | 98/18422 | 5/1998 |
| WO | 00/37016 | 6/2000 |

* cited by examiner

*Primary Examiner*—Karin Reichle
(74) *Attorney, Agent, or Firm*—Young & Thompson

(57) ABSTRACT

A product includes front fastening members, which have first regions connected to them, and back fastening members, which have second regions connected to them, with the front or back fastening members being able to receive and co-operate with the other of the front or back fastening members, respectively, and a first fastening ability being exhibited between the front and back fastening members, and the front fastening members or the back fastening members have a first extent in the longitudinal direction of the product, and the other of the front fastening members or the back fastening members, respectively, have a second extent in the longitudinal direction of the product, and exhibiting an extent ratio there between, the first regions can receive and co-operate with the back fastening members, exhibiting a second fastening ability, and/or the second regions can receive and co-operate with the front fastening members, exhibiting a third fastening ability.

20 Claims, 3 Drawing Sheets

PRODUCTS, WHICH PRODUCTS ARE ABSORBENT OR CAN ACT AS SUPPORTS FOR ABSORBENT ARTICLES

This application claims the benefit of U.S. Provisional Application 60/217,480, filed Jul. 11, 2000.

TECHNICAL FIELD

The present invention relates to a product, which product is absorbent or can act as a support for an absorbent product, with the product having a longitudinal direction, a transverse direction, an upper side and a lower side, and the product comprises a front waist section, a back waist section and a middle section which is located between the waist sections, which front waist section is provided with front fastening members and has first regions in connection with the said front fastening members, which back waist section is provided with back fastening members and has second regions in connection with said back fastening members, with the said front or back fastening members being able to receive and co-operate with the other of the said front or back fastening members, respectively, and a first fastening ability between the said front and back fastening members thereby being exhibited, and the said first fastening ability comprises a first shearing strength and a first peeling strength.

TECHNICAL BACKGROUND

Products, which products are absorbent or can act as supports for absorbent articles, which, during use, are fastened around a user's body at, for example, the waist or the hips, can, for this purpose, be provided with fastening members. The fastening members can, for example, be re-sealable tapes and an appurtenant reception zone (TLZ) consisting of reinforcing material, or a combination of hook and loop members (e.g. Velcro®). Since the cost of the fastening members, in particular the cost of the combination of hook and loop members, has constituted a considerable part of the total cost of the said products, there has been a desire to reduce the cost of the fastening members. One way of reducing this cost is to make the fastening members as small as possible. Since technical development of fastening members has resulted in a decrease in the fastening area, i.e. the contact area through which the fastening members receive and co-operate, which is required for obtaining sufficient shearing or peeling strength, it is also possible to make the fastening members small. In the present context, shearing strength denotes the ability, per unit of area, of the co-operating fastening members to withstand shearing forces, which act parallel to the said fastening area, and, in the present context, peeling strength denotes the ability, per unit of length, of the co-operating fastening members to withstand peeling forces, which act perpendicular to the said fastening area. Fastening ability is the expression that is hereinafter employed to designate shearing strength and peeling strength taken together. The fastening area which is required for sufficient fastening ability is now so small that sufficient fastening ability can be exhibited even if the fastening members only receive each other partially. This simplifies the fastening of the product due to the fact that the relatively small fastening members do not need to receive each other fully for the function of the product to be acceptable. Furthermore, the fact that the fastening members receive each other partially also provides certain possibilities for adjusting the fit of the product. However, the fact that the fastening members receive each other partially has also meant that non-activated (inactive) parts of the fastening members are exposed to their environment and consequently run the risk of catching in objects in the environment, for example the user's underclothes, bedclothes or the like, a situation which in turn increases the risk of the product being opened unintentionally.

In the case of a product in accordance with the present invention, there is no longer any risk of the parts of the fastening members which have not been received catching in objects in the environment and consequently there is no risk, either, of the product being opened unintentionally.

SUMMARY OF THE INVENTION

The present invention relates to a product, which product is absorbent or can act as a support for an absorbent article, with the product having a longitudinal direction, a transverse direction, an upper side and a lower side. Furthermore, the product comprises a front waist section, a back waist section and a middle section which is located between the waist sections, with the said front waist section being provided with front fastening members and having first regions in connection with the said front fastening members, and the said back waist section being provided with back fastening members and having second regions in connection with the said back fastening members. The said front or back fastening members can receive and co-operate with the other of the said front or back fastening members, respectively, and a first fastening ability between the said front and back fastening members is thereby exhibited, with the said first fastening ability comprising a first shearing strength and a first peeling strength. Furthermore, the said front fastening members or the said back fastening members have a first extent principally in the longitudinal direction of the product and the other of the said front fastening members or said back fastening members, respectively, have a second extent principally in the longitudinal direction of the product. An extent ratio, which extent ratio is at least 1.5, is exhibited between the said second extent and the said first extent. Furthermore, the said first regions can receive, and co-operate with, the said back fastening members, and a second fastening ability is thereby exhibited between the said first regions and the said back fastening members, and/or the said second regions can receive, and co-operate with, the said front fastening members, and a third fastening ability is thereby exhibited between the said second regions and the said front fastening members. The said second fastening ability comprises a second shearing strength and a second peeling strength, and the said third fastening ability comprises a third shearing strength and a third peeling strength. Furthermore, a first shearing strength ratio is exhibited between the said second shearing strength and the said first shearing strength, and a second shearing strength ratio is exhibited between the said third shearing strength and the said first shearing strength, both of which shearing strength ratios are less than 1.0, and a first peeling strength ratio is exhibited between the said second peeling strength and the said first peeling strength, and a second peeling strength ratio is exhibited between the said third peeling strength and the said first peeling strength, both of which peeling strength ratios are less than 10, with the said second and third shearing strengths being greater than zero the said second and third peeling strengths being greater than zero.

The said product can be an absorbent disposable product of the type which is fastened around a user's body at, for example, the waist or the hips, for example, napkins for babies or individuals who suffer from incontinence, or an absorbent or non-absorbent product of the underpants type having resealing devices on a level with the user's waist or hips. Furthermore, the said product can be an absorbent or non-absorbent product of a type in which back or front fastening members comprise a belt having fastening devices, with it being possible for the said belt to be integrated with, or separate from, the remainder of said product: see the products which are described in EP, A, 0696911. When the said product is a non-absorbent product, the said product can act as a support for an absorbent article, for example a napkin, a sanitary towel, a panty shield or an incontinence protection.

Furthermore, the longitudinal direction of the product extends from the back waist section to the front waist section, and the transverse direction of the product goes transversely to the said longitudinal direction, with the back waist section being the waist section which bears against a user's seat or back and the front waist section being the waist section which bears against a user's abdomen when using the product. The middle section which is located between the waist sections unites the two waist sections. Furthermore, when the product is being used, the upper side of the product is the side which is facing a user and its lower side is the side which is facing away from a user.

It is to be noted that the division of the said product into a back waist section, a front waist section and a middle section is not to be understood as meaning that there are boundaries between the different sections, but is first and foremost intended to facilitate the description of the said product, using as a starting point the differences which exist between the different sections depending on how they are intended to be placed in relation to a user's body. Accordingly, the transition between the different sections does not take place at any definite transverse lines but rather within diffuse transitional regions.

The said front fastening members or said back fastening members have a first extent principally in the longitudinal direction of the product, and the other of the said front fastening members or said back fastening members, respectively, have a second extent principally in the longitudinal direction of the product, with an extent ratio, which extent ratio is at least 1.5, being exhibited between the said second extent and the said first extent. Furthermore, the front and back fastening members of the product can both consist of one or more fastening members each, with it being possible for one of the said front and back fastening members to be a continuous fastening member, or it being possible for one or both of the said front or back fastening members to consist of several smaller fastening members. Furthermore, the said fastening members can have a suitable shape which is, for example a square, rectangular, circular, oval or tapering shape. The said back or front fastening members can also comprise a belt having appurtenant fastening devices, with it being possible for the said belt to be integrated with, or separate from, the remainder of said product, see the already mentioned EP, A, 0696911. Furthermore, the said front and back fastening members can have their extents substantially transverse to each other. The front and back fastening members of the product can, for example, be of the type consisting of re-sealable tapes and appurtenant reception zones (TLZ) consisting of reinforcing material, combinations of hook and loop members (for example Velcro®), hybrid variants, for example STEMWEB from 3M, fastening members which are described in GB, A, 2303821, combinations of adhesive fastening members and hook/loop members, or be of another suitable type which is known to a person skilled in the art.

The fastening member which is described in GB, A, 2303821 is a fastening member in a product in accordance with the present invention, in which the fastening member comprises a pressure-sensitive adhesive layer and an essentially incompressible, non-adhesive covering layer having a thickness which does not exceed 0.5 mm and exhibiting a multiplicity of through apertures or pores, which covering layer is applied over, and affixed to, the surface of the adhesive layer which is facing away from the product. The reciprocal distance between two adjacent apertures or pores in the covering layer does not exceed 3 mm. The said fastening member can be fastened to porous textile or textile-like surfaces but exhibits a low ability, or no ability, to adhere to smooth materials having low drapability or to itself, with the said pressure-sensitive adhesive layer consisting, for example, of hot-melt-type adhesives, other types of adhesives having suitable properties, such as water-based adhesives, hardening adhesives or adhesives containing organic solvents, or a double-sided tape, and the said covering layer consisting, for example, of a plastic net, a perforated plastic film or a layer of non-woven material or of a sparse woven fabric.

Furthermore, the said first regions in connection with the said front fastening members, and/or the said second regions, in connection with the said back fastening members, consist of a material which has a character, for example, surface structure, adhesion ability or the like, for example, non-woven materials, hot-melt-type adhesives, fibre cloths, textile materials, loop and hook materials or films, which make possible reception of, and co-operation with, the fastening members to which the regions are not connected.

The term non-woven material refers to non-woven fabrics. Suitable non-woven materials can consist of natural fibres, such as cellulose or cotton, or of synthetic fibres, such as polyethene, polypropene, polyester, polyurethane, nylon or regenerated cellulose. It is also possible to use non-woven material which is produced from fibres which include two or more components and from mixtures of different fibre types.

The said first, second and third fastening abilities are terms for the ability of the co-operating parts to withstand, per unit of area (shearing strength) and per unit of length (peeling strength), the separating forces which act on the co-operating parts when the said product is being used and is attached to a user. The co-operating parts are the front and back fastening members, the front fastening member and the said second region, and the back fastening member and the said first region, respectively. The said separating forces arise from forces which act on the co-operating parts and which tend to cause the co-operating parts to come apart, to loosen or to be moved. Furthermore, the said separating forces comprise both shearing forces and peeling forces. The term shearing forces comprises the propagated forces which act substantially tangentially to the extent of the co-operating parts and can be assumed to be parallel to the said extent. The term peeling forces comprises the propagated forces which act substantially longitudinally to the extent of the co-operating parts and can be assumed to be perpendicular to the said extent. The said first, second and third fastening abilities all consist of shearing strength (the said first, second and third shearing strength, respectively) and peeling strength (the said first, second and third peeling strength, respectively), with the said shearing strength constituting the ability of the co-operating parts to withstand, per unit of area, the said shearing forces, and the said peeling strength constituting the ability of the co-operating parts to withstand, per unit of length, the said peeling forces.

The said shearing strength can be measured by means of a pulling test in which the co-operating parts are pulled in opposite directions and substantially parallel to the extent of the co-operating parts. A method of measuring the ability to withstand shearing forces is described in detail in the U.S. Pat. No. 4,699,622, Toussant et al., and this patent is included herewith by reference in order to describe the method of measuring the shearing strength, i.e. the ability, per unit of area, of co-operating parts to withstand shearing forces.

The said peeling strength can be measured by means of a pulling test in which one of the co-operating parts is pulled from the other co-operating part at an angle which is approximately 135° with respect to the extent of the co-operating parts. A method of measuring the ability to withstand peeling forces is described in detail in the U.S. Pat. No. 4,846,815, Scripps, and this patent is included herewith by reference for the purpose of describing the method of measuring the peeling strength, i.e. the ability, per unit of length, of co-operating parts to withstand peeling forces.

The said first shearing strength and the said first peeling strength, which are exhibited when the said front and back fastening members co-operate, the said second shearing strength and the said second peeling strength, which are exhibited when the said first regions co-operate with the said back fastening members, and also the said third shearing strength and the said third peeling strength, which are exhibited when the said second regions co-operate with the said front fastening members, can all be measured using the methods which have been referred to above.

By using the said methods for measuring shearing strength and peeling strength, i.e. the fastening ability, it has been found that a product according to the present invention exhibits a first shearing strength ratio between the said second shearing strength and the said first shearing strength and also a second shearing strength ratio between the said third shearing strength and the said first shearing strength, both of which shearing strength ratios are less than 1.0, and a first peeling strength ratio between the said second peeling strength and the said first peeling strength and also a second peeling strength ratio between the said third peeling strength and the said first peeling strength, both of which peeling strength ratios are less than 10, with at least one of the said second and third shearing strengths being greater than zero and/or at least one of the said second and third peeling strengths being greater than zero.

The present invention provides further products in which the said extent ratio between the said second extent and the said first extent is at least 2, 3, 4 or 5.

The present invention furthermore provides products in which the said extent ratio between the said second extent and the said first extent is at least 10 or 15.

The present invention provides still further products in which the said extent ratio between the said second extent and the said first extent is at least 25, 30, 35, 40, 45 or 50.

In further embodiments, the present invention provides products in which the said shearing strength ratios are less than 0.8, 0.6 or 0.4.

In yet further embodiments, the present invention provides products in which the said peeling strength ratios are less than 7, 4 or 2.

In yet another embodiment, the present invention provides a product in which the said first shearing strength ratio and/or the said second shearing strength ratio is greater than 0.01, and/or the said first peeling strength ratio and/or the said second peeling strength ratio are is greater than 0.05.

Further embodiments according to the present invention provide products in which the said first shearing strength ratios and/or the said second shearing strength ratios are greater than 0.05, 0.1 or 0.2, and/or the said first peeling strength ratios and/or the said second peeling strength ratios are greater than 0.1, 0.3 or 0.5.

Yet another embodiment provides a product in accordance with the present invention in which the said first regions and the said second regions, which make possible the reception of fastening members and co-operation with these members, can be of an optional size; for example, the said first regions or the said second regions can constitute the whole of the said upper side or the whole of the said lower side, or a relatively large area of the said front waist section or the said back waist section, and/or be substantially restricted to a relatively small area. The said first regions and second regions can both consist of one, two or more part regions, and the said first regions and second regions can be homogeneous or heterogeneous.

Yet another embodiment provides a product in accordance with the present invention which comprises a first fastening area, i.e. the contact area through which the said front and back fastening members receive and co-operate, a second fastening area, i.e. the contact area through which the said first regions co-operate with the said back fastening members, and also a third fastening area, i.e. the contact area through which the said second regions co-operate with the said front fastening members. The said first, second and/or third fastening areas can be divided up into several areas which are separate from each other. The sum of the said first fastening area is less than or equal to the sum of the said second fastening area, and the sum of the said first fastening area is less than or equal to the sum of the said third fastening area.

In a product in accordance with the invention, the said front and/or back fastening member is/are arranged on projecting tongues, which projecting tongues are arranged at the said front and/or back waist section. The said projecting tongues principally extend in the transverse direction of the product.

In one embodiment, the invention provides a product in which the said first regions and/or the said second regions consist of non-woven material.

In yet another embodiment, the invention provides a product in which the lower side of a product consists of a non-woven material, which non-woven material is laminated to a liquid-impermeable layer.

One embodiment according to the invention provides a product in which the said fastening members consist of co-operating hook and loop elements.

Another embodiment according to the invention provides a product in which the said fastening members consist of co-operating, re-sealable tapes and appurtenant reception zones consisting of reinforcing material.

Yet another embodiment of the invention provides a product, which product is an absorbent product which comprises an absorbent body, with it being possible for the absorbent body to contain suitable materials which are known to a person skilled in the art, for example, natural materials, for example, cellulose fibres (for example in fluffed form), cotton fibres, peat, or similar, synthetic materials, for example, absorbent or non-absorbent synthetic fibres, super-absorbent materials, i.e. polymers having the ability to absorb several times their own weight of a fluid, or suitable mixes thereof. Furthermore, the absorbent body can also contain other components such as shape-stabilising members, liquid-spreading members, binding agents such as thermoplastic fibres, or absorbent foam material.

Yet another embodiment of the invention provides a product, which product is a non-absorbent product.

A product according to the present invention allows the front fastening members and the back fastening members to be located such that the front fastening members and the back fastening members only partially receive each other when the product is fastened, without the parts of the fastening members which have not been received being exposed to the environment of the product.

Furthermore, a product according to the present invention allows the front fastening members and the back fastening members to be located such that the front fastening members and the back fastening members only partially receive each other without there being any risk of those parts of the fastening members which have not been received catching in objects in the environment of the product, for example the user's underclothes, bedclothes or the like. The present invention thereby provides a product in which the costs of fastening members can be kept low at the same time as fastening of the product is simplified and there are certain possibilities of adjusting the fit of the product, and in which there is no risk of the product opening unintentionally.

DESCRIPTION OF THE FIGURES

Exemplary embodiments, which describe the invention but which in no way limit the invention, are described below.

DESCRIPTION OF EXEMPLARY EMBODIMENTS

Figure 1:
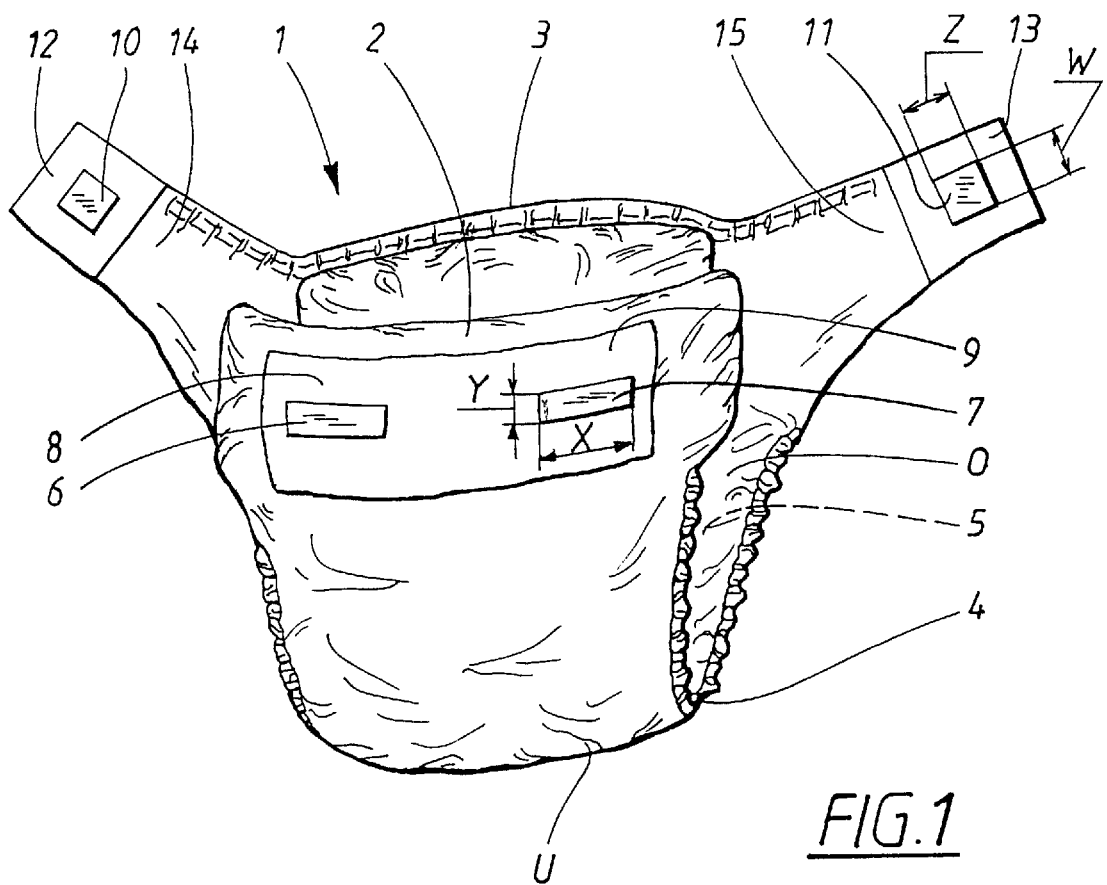
FIG. 1 is a view of a product according to the present invention seen from the front.

The product 1 shown in FIG. 1 is an incontinence protection, i.e. an absorbent product, having a longitudinal direction, a transverse direction, an upper side O, which consists of a liquid-permeable surface layer, and a lower side U which consists of a liquid-impermeable surface layer. In addition, the product 1 includes a front waist section 2, a back waist section 3, a middle section 4, which is located between the waist sections 2, 3, and an absorbent body 5 (not visible in FIG. 1), which front waist section 2 is provided with front fastening members 6, 7 and has first regions 8, 9 in connection with the said front fastening members 6, 7, and which back waist section 3 is provided with back fastening members 10, 11 and has second regions 12, 13 in connection with the said back fastening members 10, 11. In the product 1 which is described, the back fastening members 10, 11 and the associated second regions 12, 13 are arranged on projecting tongues 14, 15, which projecting tongues 14, 15 extend substantially in the transverse direction of the product.

The longitudinal direction of the product extends from the back waist section 3 to the front waist section 2, and the transverse direction of the product goes transversely with respect to the said longitudinal direction, with the back waist section 3 being the waist section which bears against the seat or back of a user and the front waist section 2 being the waist section which bears against the abdomen of a user, when the product 1 is being used.

The upper side O consists of a liquid-permeable surface layer which can, for example, be a perforated plastic film, a plastic net or a textile material, a non-woven material, or a laminate of two or more material layers of this nature. The plastic materials which are employed in liquid-permeable surface materials are usually thermoplastic materials such as polyethene or polypropene. The term non-woven material refers to non-woven fabrics. Suitable non-woven materials can consist of natural fibres, such as cellulose or cotton, or of synthetic fibres, such as polyethene, polypropene, polyester, polyurethane, nylon or regenerated cellulose. It is also possible to use non-woven materials which have been produced from fibres which include two or more components, and also mixtures of different fibre types.

The liquid-permeable surface layer in the upper side O is intended to receive liquid and conduct it into the absorption body 5. Furthermore, the said surface layer should be able to prevent so-called rewetting, that is prevent absorbed body liquid from penetrating back out of the absorption body 5.

The lower side U consists of a liquid-impermeable surface layer which can be composed of thin, liquid-impermeable plastic films. However, it is also possible to use, for the liquid-impermeable surface layer, materials which were originally liquid-permeable but which have been provided with a coating of plastic, resin or other liquid-impermeable material. This prevents liquid leaking from the lower side U of the product 1. The liquid-impermeable surface layer in the lower side U can consequently consist of any optional material which is expediently kind to the skin and which fulfils the criterion of being liquid-impermeable. Examples of materials which are suitable for use as barrier layers are plastic films, non-woven materials, for example laminated non-woven materials, and also different types of laminate. Examples of plastic films which can be used are those which consist of polyethene, polypropene or polyester.

Alternatively, the liquid-impermeable surface layer in the lower side U can consist of a laminate which is composed of a liquid-permeable plastic layer which faces the absorption body and a non-woven layer which faces the underclothes of the user. Suitable non-woven materials can consist of natural fibres, such as cellulose or cotton, or of synthetic fibres, such as polyethene, polypropene, polyester, polyurethane, nylon or regenerated cellulose. It is also possible to use non-woven materials which have been produced from fibres which include two or more components and also from mixtures of different fibre types. Such a construction provides a leakage-safe barrier layer having a textile feel and also makes possible reception, and a certain co-operation, between the non-woven material, which should then include the regions 8, 9, and also 12, 13, and the fastening members 10, 11, and also 6, 7.

The absorption body 5 can advantageously be substantially made up of cellulose fluff pulp. The cellulose fluff pulp can be present in the form of coils, bundles or sheets which are dry-defibred and converted, in fluffed form, into a pulp mat with or without the admixture of super-absorbent materials, i.e. polymers having the ability to absorb several times their own weight of a fluid. Other utilisable natural materials can be cotton fibres, peat or similar. Utilisable synthetic materials can be absorbent or non-absorbent synthetic fibres. Furthermore, the absorbent body can also contain other components such as shape-stabilising members, liquid-spreading members, binding agents such as thermoplastic fibres, or absorbent foam materials. The absorption body 5 can also consist of optional and suitable mixtures, which are known to a person skilled in the art, of the materials and components which are enumerated here. Furthermore, the absorption body 5 can consist of a continuous layer or be made up of several different layers or parts. The absorption body 5 can, in addition, be profiled, i.e. be of different thicknesses in different parts of the product 1.

The layers which constitute the upper side O and the lower side U are connected to each other outside the absorption body 5 and around the whole of the periphery of the product 1. The said layers can be joined together in any optional and suitable manner, for example by means of gluing, sewing or welding using heat or ultrasound.

The division of the product 1 into two waist sections 2, 3 and a middle section 4 is not to be understood as meaning that there are boundaries between the different sections 2–4, but is first and foremost intended to facilitate description of the product 1, using as the point of departure the differences which exist between the different sections 2–4 depending on how they are intended to be located in relation to a user's body. Consequently, the transition between the different sections 2–4 does not take place at definite transverse lines but rather within diffuse transitional regions.

The front and back fastening members 6, 7, 10, 11 of the product can, for example, be of the type comprising re-sealable tapes and appurtenant reception zones (TLZ) consisting of reinforcing material, combinations of hook and loop members (for example Velcro®), hybrid variants, for example STEMWEB from 3M, fastening members which are described in GB, A, 2303821, or combinations of adhesive fastening members and hook/loop members, or be of another suitable type which is known to a person skilled in the art.

The front fastening members shown in FIG. 1, i.e. 6 and 7, have an extent, X, which is substantially in the transverse direction of the product, and a first extent, Y, which is substantially in the longitudinal direction of the product. Furthermore, the back fastening members, 10 and 11, also shown in FIG. 1, have an extent, Z, which is substantially in the transverse direction of the product, and a second extent, W, which is substantially in the longitudinal direction of the product.

Furthermore, the said first regions 8, 9, in connection with the said front fastening members 6, 7, and/or the said second regions 12, 13, in connection with the said back fastening members 10, 11, consist of a material which has a character, for example surface structure, adhesion ability or the like, for example non-woven materials, hot-melt-type adhesives, fibre cloths, textile materials, loop and hook materials or films, which make possible reception of, and a certain co-operation with, the fastening members to which the regions are not connected.

When said front and back fastening members 6, 7, 10, 11 co-operate, a fastening ability, F1, is exhibited, which fastening ability consists of the said first shearing strength, S1, and the said first peeling strength, P1. The said shearing strength, S1, can be measured by the previously mentioned method in the U.S. Pat. No. 4,699,622, Toussant et al., and the said peeling strength, P1, can be measured by the previously mentioned method in the patent U.S. Pat. No. 4,846,815, Scripps.

The said second shearing strength, S2, and the said second peeling strength, P2, both constituting the said fastening ability, F2, which is exhibited when the said first regions, 8 and 9, co-operate with the said back fastening members, 10 and 11, and also the said third shearing strength, S3, and the said third peeling strength, P3, both constituting the said third fastening ability, F3, which is exhibited when the said second regions, 12 and 13, co-operate with the said front fastening members, 6 and 7, can also be measured using the above mentioned methods.

By using the said methods for measuring shearing strength and peeling strength, i.e. fastening ability, it has been found that a product, 1, in accordance with the present invention exhibits a first shearing strength ratio, S2/S1, between the said second shearing strength, S2, and the said first shearing strength, S1, and also a second shearing strength ratio, S3/S1, between the said third shearing strength, S3, and the said first shearing strength, S1, both of which shearing strength ratios, S2/S1 and S3/S1, are less than 1.0, and a first peeling strength ratio, P2/P1, between the said second peeling strength, P2, and the said first peeling strength, P1, and also a second peeling strength ratio, P3/P1, between the said third peeling strength, P3, and the said first peeling strength, P1, both of which peeling strength ratios, P2/P1 and P3/P1, are less than 10, with at least one of the said second and third shearing strengths, S2 and S3, being greater than zero and/or at least one of the said second and third peeling strengths, P2 and P3, being greater than zero.

Figure 2:
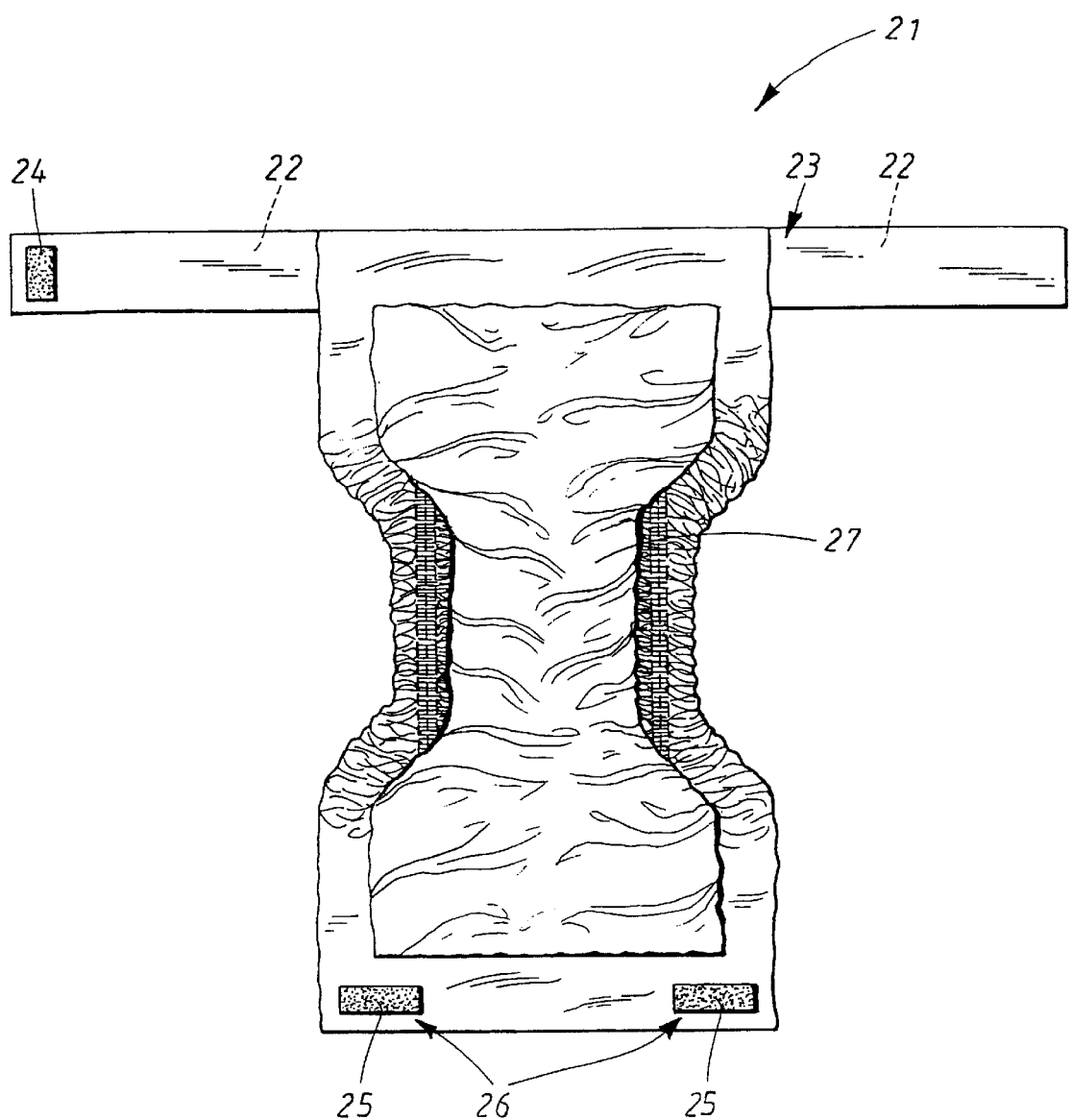
FIG. 2 is a view of yet another product according to the present invention, which product is seen from above and is spread out flat.

The product 21 shown in FIG. 2 describes yet another type of product according to the present invention, which product is an absorbent garment in which back fastening members 22 (not shown in FIG. 2) are located on a belt 23 which is integrated with the absorbent garment. The integrated belt 23 has a fastening device 24 at one end of the belt, which fastening device 24 is for fastening the belt 23 to itself. In addition, the product 21 includes front fastening members 25, first regions 26 in connection with the said front fastening members 25, and absorbent material 27. The product 21 also includes back fastening members 22 (not shown in FIG. 2) and second regions (not shown in FIG. 2) in connection with the said back fastening members 22. When the belt 23 is fastened to itself by the fastening device 24 being fastened to the belt 23, the said front fastening members 25 can in turn be fastened to the belt 23, with the product 21 being fastened on a user. For a more detailed description of a product according to the present invention it is referred to the description of product 1 in accordance with FIG. 1.

Figure 3:
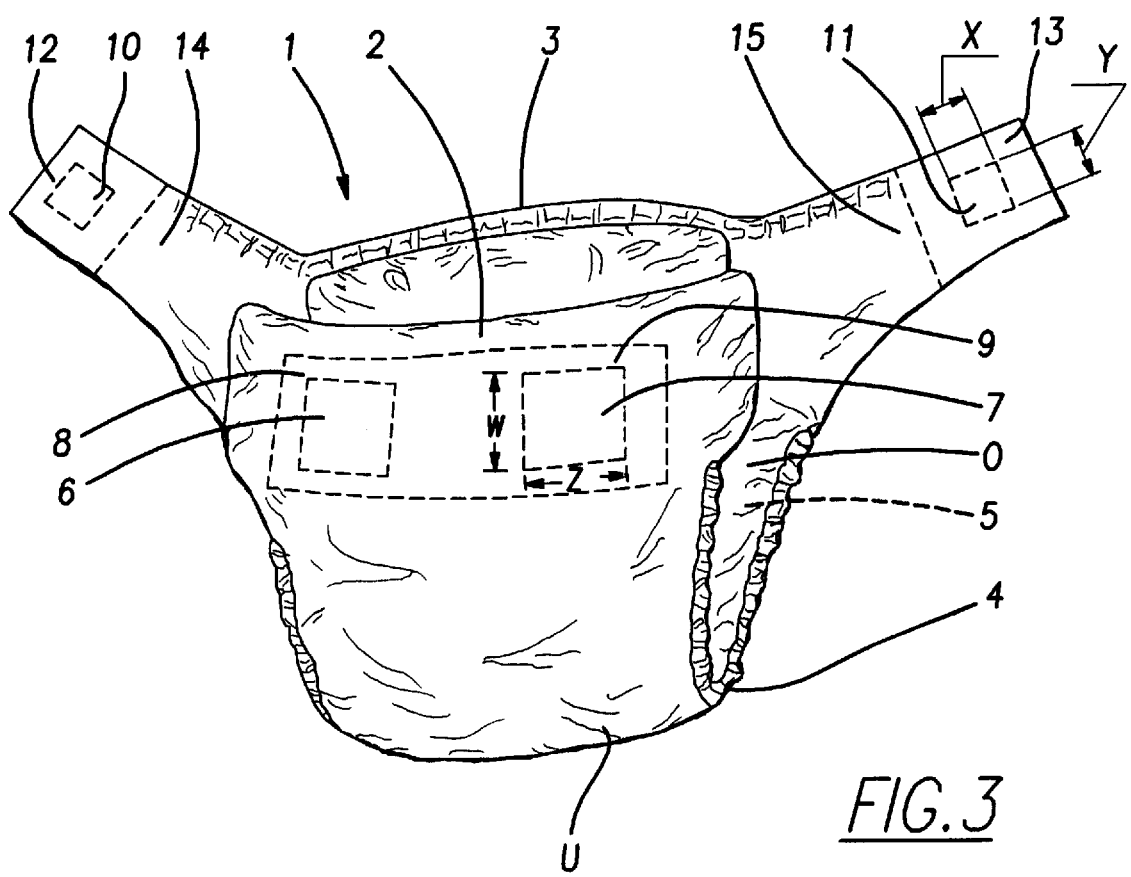
FIG. 3 is a view of a different product according to the present invention seen from the front.

The product shown in FIG. 3 has the front fastening members 6, 7 and first regions 8, 9 on the upper side O and the back fastening members 10, 11 and second regions 12, 13 on the lower side U. The product of FIG. 3 also illustrates the back fastening members having the first extent Y and the front fastening members having the second extent W.

What is claimed is:

1. A product for fastening around a user's body to enable absorption having a longitudinal direction, a transverse direction, an upper side and a lower side, the product comprising a front waist section, a back waist section, and a middle section which is located between the waist sections, which front waist section is provided with front fastening members and has first regions in connection with said front fastening members, which back waist section is provided with back fastening members and has second regions in connection with said back fastening members, said front or back fastening members being able to receive and cooperate with the other of said front or back fastening members, respectively, for fastening the product around the user's body, and a first fastening ability being exhibited between said front and back fastening members, said first fastening ability comprising a first shearing strength and a first peeling strength, and said front fastening members have a first extent substantially in the longitudinal direction of the product and said back fastening members have a second extent substantially in the longitudinal direction of the product, wherein said first regions and front fastening members or said second regions and back fastening members are present on said upper side and the other of said first regions and front fastening members or said second regions and back fastening members are present on said lower side and an extent ratio is exhibited between said second extent and said first extent, with the extent ratio being at least 1.5, wherein said first regions can receive and cooperate with inactive parts of said back fastening members, and a second fastening ability is exhibited between said first regions and said back fastening members, said second fastening ability comprising a second shearing strength and a second peeling strength, wherein said second regions can receive and cooperate with inactive parts of said front fastening members, and a third fastening ability is exhibited between said second regions and said front fastening members, said third fastening ability comprising a third shearing strength and a third peeling strength, wherein a first shearing strength ratio is exhibited between said second shearing strength and said first shearing strength, a second shearing strength ratio is exhibited between said third shearing strength and the first shearing strength, both of which shearing strength ratios are less than 1.0 and said second and third shearing strengths being greater than zero, and wherein a first peeling strength ratio is exhibited between said second peeling strength and said first peeling strength, a second peeling strength ratio is exhibited between said third peeling strength and said first peeling strength, both of which peeling strength ratios are less than 10, and said second and third peeling strengths being greater than zero.

2. The product according to claim 1 wherein said product includes at least one of: said shearing strength ratios being less than 0.8, and said peeling strength ratios being less than 7.

3. The product according to claim 1 wherein at least one of said first shearing strength ratio and said second shearing strength ratio is greater than 0.01, and at least one of said first peeling strength ratio and said second peeling strength ratio is greater than 0.05.

4. The product according to claim 1, wherein at least one of said front and back fastening members is arranged on projecting tongues, which projecting tongues are arranged on the respective one of said front and back waist sections.

5. The product according to claim 1, wherein at least one of said first regions and said second regions consist of non-woven material.

6. The product according to claim 1, wherein said lower side consists of non-woven material, which non-woven material is laminated to a liquid-impermeable layer.

7. The product according to claim 1 wherein said fastening members consist of cooperating hook and loop elements.

8. The product according to claim 1 wherein said fastening members consist of cooperating re-sealable tapes and appurtenant reception zones consisting of reinforcing material.

9. The product according to claim 1, wherein said product an absorbent product, absorbent includes an absorbent body.

10. The product according to claim 1, wherein said product includes a non-absorbent support for an absorbent body.

11. A product for fastening around a user's body to enable absorption having a longitudinal direction, a transverse direction, an upper side and a lower side, the product comprising a front waist section, a back waist section, and a middle section which is located between the waist sections, which front waist section is provided with front fastening members and has first regions in connection with said front fastening members, which back waist section is provided with back fastening members and has second regions in connection with said back fastening members, said front or back fastening members being able to receive and cooperate with the other of said front or back fastening members, respectively, for fastening the product around the user's body, and a first fastening ability being exhibited between said front and back fastening members, said first fastening ability comprising a first shearing strength and a first peeling strength, and said back fastening members have a first extent substantially in the longitudinal direction of the product and said front fastening members have a second extent substantially in the longitudinal direction of the product, wherein said first regions and front fastening members or said second regions and back fastening members are present on said upper side and the other of said first regions and front fastening members or said second regions and back fastening members are present on said lower side and an extent ratio is exhibited between said second extent and said first extent, with the extent ratio being at least 1.5, wherein said first regions can receive and cooperate with inactive parts of said back fastening members, and a second fastening ability is exhibited between said first regions and said back fastening members, said second fastening ability comprising a second shearing strength and a second peeling strength, wherein said second regions can receive and cooperate with inactive parts of said front fastening members, and a third fastening ability is exhibited between said second regions and said front fastening members, said third fastening ability comprising a third shearing strength and a third peeling strength, wherein a first shearing strength ratio is exhibited between said second shearing strength and said first shearing strength, a second shearing strength ratio is exhibited between said third shearing strength and the first shearing strength, both of which shearing strength ratios are less than 1.0 and said second and third shearing strengths being greater than zero, and wherein a first peeling strength ratio is exhibited between said second peeling strength and said first peeling strength, a second peeling strength ratio is exhibited between said third peeling strength and said first peeling strength, both of which peeling strength ratios are less than 10, and said second and third peeling strengths being greater than zero.

12. The product according to claim 11 wherein said product includes at least one of: said shearing strength ratios being less than 0.8, and said peeling strength ratios being less than 7.

13. The product according to claim 11, wherein at least one of said first shearing strength ratio and said second shearing strength ratio is greater than 0.01, and at least one of said first peeling strength ratio and said second peeling strength ratio is greater than 0.05.

14. The product according to claim 11 wherein at least one of said front and back fastening members is arranged on projecting tongues, which projecting tongues are arranged on the respective one of said front and back waist sections.

15. The product according to claim 13, wherein at least one of said first regions and said second regions consist of non-woven material.

16. The product according to claim 11, wherein said lower side consists of non-woven material, which non-woven material is laminated to a liquid-impermeable layer.

17. The product according to claim 11, wherein said fastening members consist of cooperating hook and loop elements.

18. The product according to claim 11, wherein said fastening members consist of cooperating re-sealable tapes and appurtenant reception zones consisting of reinforcing material.

19. The product according to claim 11, wherein said product an absorbent product, absorbent includes an absorbent body.

20. The product according to claim 11, wherein said product includes a non-absorbent support for an absorbent body.

* * * * *